United States Patent [19]

Wehner et al.

[11] Patent Number: 4,727,104
[45] Date of Patent: Feb. 23, 1988

[54] NOVEL TRIAZOLE DERIVATIVES AND THE USE THEREOF FOR STABILIZING ORGANIC POLYMERS

[75] Inventors: Wolfgang Wehner, Zwingenberg; Klaus-Peter Michaelis, Lindenfels/Odenwald; Rainer Schneider, Zwingenberg, all of Fed. Rep. of Germany

[73] Assignee: Ciba-Geigy Corporation, Ardsley, N.Y.

[21] Appl. No.: 822,432

[22] Filed: Jan. 27, 1986

[30] Foreign Application Priority Data

Jan. 29, 1985 [CH] Switzerland ............ 387/85
Feb. 19, 1985 [CH] Switzerland ............ 754/85

[51] Int. Cl.$^4$ .................. C08K 5/34; C07D 249/10
[52] U.S. Cl. ..................... 524/106; 548/266; 524/114; 524/147; 524/153; 524/398; 524/399; 524/400
[58] Field of Search ............ 524/106, 114, 147, 153, 524/398, 399, 400; 548/266

[56] References Cited

U.S. PATENT DOCUMENTS

| | | | |
|---|---|---|---|
| 2,985,619 | 5/1961 | Roos et al. | 524/106 |
| 3,673,152 | 6/1972 | Minagawa et al. | 252/401 |
| 3,843,633 | 10/1974 | Weber et al. | 524/106 |
| 3,880,841 | 4/1975 | Fleck et al. | 524/106 |
| 4,223,031 | 9/1980 | Covington et al. | 424/251 |
| 4,491,587 | 1/1985 | Covington et al. | 424/269 |
| 4,615,970 | 10/1986 | Kojima et al. | 548/266 |
| 4,628,103 | 12/1986 | Alicot | 548/266 |

FOREIGN PATENT DOCUMENTS

| | | | |
|---|---|---|---|
| 3048659 | 9/1981 | Fed. Rep. of Germany. | |
| 0017559 | 2/1977 | Japan | 524/106 |
| 2170203A | 7/1986 | United Kingdom | 548/266 |

OTHER PUBLICATIONS

Chemical Abstracts, vol. 58, 9077c.
L. A. Williams, J. Chem. Soc., 1962, 2222.

Primary Examiner—Morton Foelak
Assistant Examiner—Kriellion Morgan
Attorney, Agent, or Firm—Edward McC. Roberts; Luther A. R. Hall

[57] ABSTRACT

Compounds of formula I

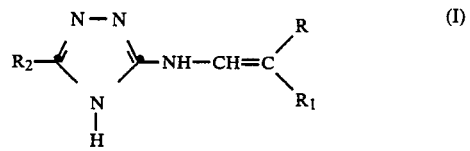

wherein R is —COOCH$_3$, —COOC$_2$H$_5$ or methyl, R$_1$ is —COOR$_3$, R$_2$ is hydrogen, methyl or ethyl and R$_3$ is C$_1$–C$_{22}$alkyl, are suitable for stabilizing organic polymers, in particular chlorinated thermoplastics, against the influence of heat and/or light.

15 Claims, No Drawings

NOVEL TRIAZOLE DERIVATIVES AND THE USE THEREOF FOR STABILIZING ORGANIC POLYMERS

The present invention relates to novel 3-(vinylamino)-1,2,4-triazole derivatives and to the use thereof for stabilising organic polymers, in particular chlorinated thermoplastics, against the influence of heat and/or, in particular, of light.

The use of 3-amino-1,2,4-triazoles for stabilising PVC against the influence of heat and light is known from U.S. Pat. No. 2,985,619 and German Offenlegungsschrift No. 30 48 659. It has been found, however, that these known stabilisers for PVC do not always satisfy the exacting demands of actual practice. 3-(dinitrilevinylamino)-1,2,4-triazoles are described in German Offenlegungsschrift No. 29 18 085 as intermediates for the preparation of pharmaceutically effective azolopyrimidinones.

Surprisingly, it has now been found that specific 3-(vinylamino)-1,2,4-triazole derivatives are most suitable for stabilising organic polymers, in particular chlorinated thermoplastics, against the influence of heat and, in particular, of light.

Accordingly, the present invention relates to compounds of formula I

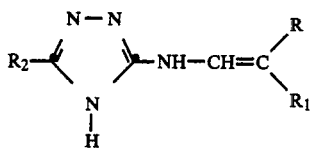

wherein R is $-COOCH_3$, $-COOC_2H_5$ or methyl, $R_1$ is $-COOR_3$, $R_2$ is hydrogen, methyl or ethyl and $R_3$ is $C_1-C_{22}$alkyl. $R_3$ as $C_1-C_{22}$alkyl is straight chain or branched alkyl, e.g. methyl, ethyl, n-propyl, isobutyl, n-butyl, sec-butyl, tert-butyl, n-pentyl, n-hexyl, 2-ethylhexyl, n-heptyl, n-octyl, 1,1,3,3-tetramethylbutyl, n-decyl, undecyl, dodecyl, tridecyl, tetradecyl, pentadecyl, hexadecyl, octadecyl, eicosyl, heneicosyl or docosyl, with methyl and ethyl being preferred.

Compounds of formula I wherein $R_2$ is hydrogen are of particular interest.

Preferred compounds of formula I are those wherein $R_2$ is hydrogen and $R_3$ is $C_1-C_{14}$alkyl, preferably methyl or ethyl.

The compound of formula II $$\begin{array}{c} N-N \\ \diagup \diagdown \\ \diagdown \diagup -NH-CH=C \diagup^{COOC_2H_5}_{COOC_2H_5} \\ N \\ | \\ H \end{array} \quad (II)$$

is particularly preferred and those of formula III $$\begin{array}{c} N-N \\ \diagup \diagdown \\ \diagdown \diagup -NH-CH=C \diagup^{CH_3}_{COOR_3} \\ N \\ | \\ H \end{array} \quad (III)$$

wherein $R_3$ is methyl, ethyl, n-butyl, isobutyl, 2-ethylhexyl or isotridecyl, are most preferred.

The compounds of formula I can be prepared by methods analogous to generally known ones:

If R is methyl, by reacting an amine of formula IV $$\begin{array}{c} N-N \\ R_2 \diagup \diagdown \\ \diagdown \diagup -NH_2 \\ N \\ | \\ H \end{array} \quad (IV)$$

with an aldehyde of formula V $$O=CH-C\diagup^{R}_{R_1} \quad (V)$$

and, if R is $-COOCH_3$ or $-COOC_2H_5$, by reacting an amine of formula IV with a vinyl ether of formula VI $$R_4O-CH=C\diagup^{R}_{R_1} \quad (VI)$$

wherein $R_4$ is methyl or ethyl.

The starting materials of formulae IV, V and VI are known. Those compounds which are novel can be prepared by methods analogous to generally known ones.

As mentioned at the outset, the compounds of formula I are very effective for improving the heat and, in particular, light stability of synthetic polymers such as the following:

1. Polymers of monoolefins and diolefines, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefines with each other or with other vinyl monomers, such as ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or α-methylstyrene with dienes or acrylic derivatives, such as styrene/butadiene, styrene/acrylonitrile, styrene/alkyl methacrylate, styrene/maleic anhydride, styrene/acrylonitrile/methyl acrylate; mixtures of high impact strength from styrene copolymers and another polymer, such as from a polyacrylate, a diene polymer or an ethylene/propylene/diene terpolymer; and block copolymers of styrene, such as styrene/butadiene/styrene, styrene/isoprene/styrene, styrene/ethylene/- butylene/styrene or styrene/ethylene/propylene/styrene.

6. Graft copolymers of styrene, such as styrene on polybutadiene, styrene and acrylonitrile on polybutadiene, styrene and maleic anhydride on polybutadiene, styrene and alkyl acrylates or methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, in particular polymers from halogen-containing vinyl compounds such as polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitriles.

9. Copolymers from the monomers mentioned under (8) with each other or with other unsaturated monomers, such as acrylonitrile/butadiene, acrylonitrile/alkyl acrylate, acrylonitrile/alkoxyalkyl acrylate or acrylonitrile/vinyl halide copolymers or acrylonitrile-/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain comonomers such as ethylene oxide.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamid or poly-m-phenylene isophthalamide, as well as block-copolymers thereof with polyethers, such as with polyethylene glycol, polypropylene glycol or polytetramethylene glycols.

16. Polyureas, polyimides, polyamide-imides and polybenzimidazoles.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, polyhydroxybenzoates as well as block-polyether-esters derived from polyethers having hydroxyl end groups.

18. Polycarbonates and polyester-carbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Crosslinkable acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

The stabilisers of the invention are incorporated into the polymers singly or in admixture with one another in amounts of 0.01 to 5% by weight, based on the stabilised material.

The stabiliser substances are incorporated into the organic polymers by known methods. The addition can take place at any processing stage before moulding. The stabiliser may be mixed with the pulverulent polymers, or an emulsion or suspension of the stabiliser may be mixed with a solution, suspension or emulsion of the polymer.

The materials thus stabilised can be employed in a large variety of forms, e.g. as sheets, filaments, ribbons, moulding compositions or profiles or as binders for varnishes, adhesives or cements.

On application, the compounds of formula I may be employed together with other stabilisers. Examples of further additives with which the compounds of the invention may be employed are those additives listed in European published patent application No. 0 114 148, pp. 10–15.

The compounds of the present invention are suitable preferably for protecting chlorinated thermoplastics against heat-induced and, in particular, light-induced degradation. They may be incorporated into the thermoplastics to be stabilised singly or in admixture with one another, before processing by conventional methods, and in respective amounts of 0.1 to 5% by weight, preferably 0.2 to 1.5% by weight, based on the entire composition.

A still better stabilising action is obtained by additionally using customary amounts of one of the conventional PVC stabilisers and/or additives such as epoxy compounds, preferably epoxidised fatty acid esters such as epoxidised soybean oil, phosphites, organometal compounds of the second main and auxiliary group of the Periodic Table, e.g. metal carboxylates, in particular salts of carboxylic acids containing 8 to 20 carbon atoms, e.g. calcium stearate or zinc stearate, or metal phenolates of phenols containing 6 to 20 carbon atoms, e.g. p-tert-butylphenol, basic salts of metals of the second to fourth main and auxiliary groups of the Periodic Table, e.g. basic lead sulfate, lead carboxylates or aluminium oxide, organotin compounds, in particular mixtures of mono- and diorganotin compounds, e.g. n-octyltin tris[isooctyl thioglycolate], di-n-octyltin bis[isooctyl thioglycolate], dibutyltin sulfide, dibutyltin thioglycolate or butyltin sulfide, as well as methyltin tris[alkyl thioglycolate], n-butyltin tris[alkyl thioglycolate], carbo-n-butoxyethyltin tris[alkyl thioglycolate], bis[methyl]tin bis[alkyl thioglycolate], bis[n-butyl]tin bis[alkyl thioglycolate], bis[carbo-n-butoxyethyl]tin bis[alkyl thioglycolate], methyltin tris[alkyl thiopropionate], n-butyltin tris[alkyl thiopropionate], carbo-n-butoxyethyltin tris[alkyl thiopropionate], bis[methyl]tin bis[alkyl thiopropionate], bis[n-butyl]tin bis[alkyl thiopropionate], bis[carbo-n-butoxyethyl]tin bis[alkyl thiopropionate], with alkyl meaning for example 2-ethylhexyl, dodecyl, tridecyl or tetradecyl, and also organotin carboxylates, in particular maleates or hemiester maleates, or organic antimony compounds such as antimony tris[isooctyl thioglycolate](isooctyl=2-ethylhexyl), nitrogen-containing stabilisers such as aminocrotonates, α-phenylindoles, aminobenzamides, aminobenzosulfonamides, as well as pyrroles such as those described for example in European Pat. No. 22 087 and in British Pat. No. 2 078 761, or cynamide, dicyanamide and guanamines such as benzoguanamine, ureas and thioureas such as monophenylurea or diphenylurea, uraciles such as those described in European patent application No. 65 934, thiouraciles such as those disclosed in European patent application No. 41 479, 1,3-diketo compounds such as those described e.g. in European patent application No. 35 268, thiophosphates such as those described in European patent application No. 90 770 and thiophosphites such as those described in U.S. Pat. No. 2,824,847, mercaptanes such as thioglycolpropionates and β-mercaptopropionates such as those disclosed for example in European patent application No. 22 047, as well as organosilicon mercaptides derived therefrom, polyols such as pentaerythrit, dipentaerythrit, trimethylolpropane or the partial esters thereof, and also antioxidants, light stabilisers, pigments and lubricants.

Co-stabilisers are preferably incorporated in amounts of 0.05 to 6% by weight, most preferably 0.1 to 3% by weight, based on the entire composition. The ratio of the compounds of this invention to co-stabilisers may be from about 2:1 to 1:8, Phosphites which are particularly suitable as co-stabilisers are for example those described in European patent application No. 65 934, pp. 5 and 6, as well as e.g. tetraphenyldipropyleneglycol diphosphite and poly(dipropyleneglycol)phenyl phosphite.

A particularly good stabilising action is obtained by adding to the compounds of formula I at least one epoxy compound and/or metal carboxylate or metal phenolate of a metal of the second main group of the Periodic Table, preferably a calcium carboxylate, most preferably calcium stearate. A still better stabilising action is obtained by using additionally at least one of the above-mentioned phosphites or at least one zinc or cadmium carboxylate or organotin compound.

The best stabilising action is obtained, however, by stabilising the chlorinated thermoplastics with a mixture of at least one compound of formula I, at least one epoxy compound and/or metal carboxylate or metal phenolate of a metal of the second main group of the Periodic Table, at least one zinc carboxylate or cadmium carboxylate or organotin compound, and at least one of the above-mentioned phosphites.

Preferred chlorinated thermoplastics to be stabilised are vinyl chloride polymers or copolymers. Suspension and mass polymers, and emulsion polymers having a low content of emulsifier, are preferred. Examples of suitable comonomers for the copolymers are: vinyl acetate, vinylidene chloride, trans-dichloroethylene, ethylene, propylene, butylene, maleic acid, acrylic acid, fumaric acid and itaconic acid. Further suitable chlorinated polymers are post-chlorinated PVC and chlorinated polyolefins, as well as graft polymers of PVC with EVA and MBS.

Particularly preferred materials to be stabilised with compounds of formula I are PVC materials for outside use (e.g. window frame profiles or sidings or sheets) as well as transpaent PVC. An effective stabilisation of PVC can be achieved with the compounds of the invention also during and after γ-irradiation.

Accordingly, the invention also relates to thermoplastic moulding compositions based on vinyl chloride polymers or copolymers and containing 0.1 to 5.0% by weight of a compound of formula I.

The thermoplastics stabilised according to the invention are obtained by known methods by incorporating the stabilisers and, if desired, further additives, into the polymer. A homogeneous mixture of stabiliser and PVC can be obtained e.g. by using a two-roll mixer in the temperature range from 150° to 210° C. Depending on the end use of the moulding composition, further additives may also be incorporated before or simultaneously with the incorporation of the stabiliser. Examples of further additives are: lubricants (preferably montan waxes or glycerol esters), fatty acid esters, paraffins, plasticisers, fillers, carbon black, asbestos, kaolin, talcum, glass fibres, modifiers (such as impact strength additives), fluorescent whitening agents, pigments, light stabilisers, UV absorbers, flame retardants, antistats or further co-stabilisers, e.g. antioxidants, in particular phenolic antioxidants. The thermoplastic moulding compositions obtained according to the invention can be processed to moulded articles by conventional moulding methods, e.g. by extrusion, injection moulding or calendering. The use of the moulding compositions as plastisols is also possible.

The stabilisers employed in the practice of this invention effect excellent heat stabilisation and, in particular, excellent light stabilisation of the thermoplastic moulding compositions obtained.

The invention is illustrated in more detail by the following Examples. Parts and percentages are by weight, unless otherwise stated.

EXAMPLE 1

A reaction vessel is charged with 126.1 parts (1.5 moles) of 3-amino-1,2,4-triazole in 500 ml of boiling methanol and then, with stirring, 174.2 parts (1.5 moles) of methyl α-formylpropionate are added slowly to this solution. After boiling for 3 hours under reflux, the methanolic solution is concentrated to half its volume and then cooled.

The precipitated crystals are isolated by suction filtration, washed with a small amount of cold alcohol and then dried to constant weight. Yield: 207 parts (87% of theory) of the chemically pure product of the formula

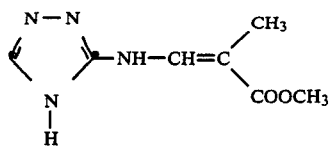

with a melting point of 205° C.

In place of methanol, a solvent selected from the following may be employed: ethanol, propanol, isopropanol, butanols, cyclic ethers, glycol hemiesters and diethers as well as acid amides or alkylated acid amides.

EXAMPLES 2-8

The compounds of this invention listed in Table 1 below are obtained by a procedure analogous to that described in Example 1 using the corresponding starting materials and solvents.

TABLE 1

N—N, NH—CH=C with CH$_3$ and COOR$_3$ groups (triazole structure)

| Example | R$_3$ | Solvent | m.p. | Yield |
|---|---|---|---|---|
| 2 | CH$_3$ | isopropanol | 205° C. | 80% |
| 3 | n-C$_4$H$_9$ | tetrahydrofuran | 158–159° C. | 82% |
| 4 | CH$_2$—CH(C$_2$H$_5$)—C$_4$H$_9$ | tetrahydrofuran | 121° C. | 68% |
| 5 | i-C$_4$H$_9$ | tetrahydrofuran | 160–162° C. | 64% |
| 6 | t-C$_4$H$_9$ | tetrahydrofuran | 172–173° C. | 84% |
| 7 | n-C$_{12}$H$_{25}$ | tetrahydrofuran | 114–116° C. | 70% |
| 8 | i-C$_{13}$H$_{27}$ | tetrahydrofuran | resin | acc. to H$^1$NMR 90% |

EXAMPLE 9

The compound of the formula

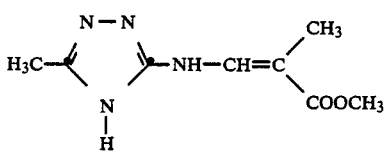

is prepared by a procedure analogous to that described in Example 1. 3-Amino-5-methyl-1,2,4-triazole is used in place of 3-amino-1,2,4-triazole. The yield is 20% of theory and the melting point is 177°–178° C.

EXAMPLE 10

A reaction vessel is charged with 50.4 parts (0.6 mole) of 3-amino-1,2,4-triazole in 200 parts of boiling ethanol and then, with stirring, 129.0 parts (0.6 mole) of diethyl ethoxymethylenemalonate are added slowly to this solution. After boiling for 3 hours under reflux, the ethanolic solution is concentrated to half its volume and then cooled. The precipitated crystals are isolated by suction filtration, washed with a small amount of cold ethanol and then dried to constant weight. Yield: 49.0 parts (32% of theory) of the chemically pure product of the formula

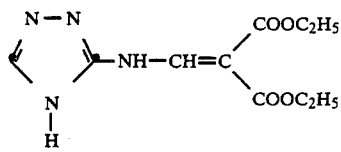

with a melting point of 194°–195° C.

The same product with the same melting point is obtained in the same yield if isopropanol is employed as solvent in place of ethanol.

EXAMPLE 11

(Thermostabilising action in PVC)

A dry blend consisting of one of the formulations indicated in Tables 2 to 4 below is rolled for 5 minutes at 180° C. on a roller mill. Samples taken from the rolled sheet obtained (thickness=0.3 mm) are subject to heat in a test oven at 180° C., and at the intervals indicated the thermal ageing of a sample is determined according to the Yellowness Index (YI) of ASTM D 1925-70. The results are shown in the following Tables 2 to 4.

TABLE 2

| S-PVC (K value 64) | 100 parts | | | |
|---|---|---|---|---|
| epoxidised soybean oil | 2 parts | | | |

| Additive of the invention | YI after thermal ageing (minutes) | | | | |
|---|---|---|---|---|---|
| | 0 | 10 | 20 | 30 | 40 |
| none | 42.0 | 91.0 | 114.0 | 138.0 | — |
| compound of Ex. 1 1.5 parts | 1.8 | 7.0 | 16.4 | 51.4 | — |
| compound of Ex. 2 0.6 part* | 8.3 | 20.4 | 42.2 | 59.0 | 104.0 |
| compound of Ex. 3 0.7 part* | 8.7 | 28.3 | 58.7 | 94.5 | — |
| compound of Ex. 4 1.5 parts | 15.4 | 21.8 | 36.8 | 54.3 | 87.0 |
| compound of Ex. 5 1.5 parts | 11.4 | 14.4 | 23.3 | 45.1 | 75.7 |
| compound of Ex. 6 1.5 parts | 10.2 | 20.2 | 37.1 | 64.1 | 126.9 |
| compound of Ex. 7 1.5 parts | 18.1 | 24.2 | 46.7 | 56.9 | 81.0 |
| compound of Ex. 8 1.5 parts | 19.7 | 32.6 | 46.8 | 66.2 | 97.1 |
| compound of Ex. 9 1.5 parts | 26.7 | 39.7 | 67.7 | 110.8 | — |

*corresponds to a weight-in quantity of 2.5 mmole

TABLE 3

| S-PVC (K value 64) | 100 parts | | | | | | |
|---|---|---|---|---|---|---|---|
| epoxidised soybean oil | 3 parts | | | | | | |
| calcium stearate | 0.35 part | | | | | | |
| zinc stearate | 0.15 part | | | | | | |

| Additive of the invention | YI after thermal ageing (minutes) | | | | | | |
|---|---|---|---|---|---|---|---|
| | 0 | 5 | 10 | 15 | 20 | 25 | 30 | 35 |
| none | 36.3 | 51.2 | 45.7 | 53.4 | 62.4 | 88.4 | 103.9 | — |
| compound of Ex. 1 0.5 part | 7.1 | 11.5 | 14.9 | 27.0 | 33.0 | 48.0 | 62.0 | 93.0 |

TABLE 4

| | S-PVC (K value 64) | | | 100 parts | | | | | |
|---|---|---|---|---|---|---|---|---|---|
| | epoxidised soybean oil | | | 3 parts | | | | | |
| | didecylphenyl phosphite | | | 0.55 part | | | | | |
| | calcium stearate | | | 0.35 part | | | | | |
| | zinc stearate | | | 0.15 part | | | | | |

| Additive of the invention | YI after thermal ageing (minutes) | | | | | | | | | |
|---|---|---|---|---|---|---|---|---|---|---|
| | 0 | 5 | 10 | 15 | 20 | 25 | 30 | 35 | 40 | 45 |
| none | 18.2 | 33.8 | 36.7 | 39.3 | 38.5 | 38.2 | 38.7 | 59.4 | 93.1 | 112.5 |
| compound of Ex. 2 0.6 part | 4.4 | 6.4 | 10.1 | 11.8 | 18.5 | 23.3 | 29.7 | 54.1 | 66.8 | 79.9 |
| compound of Ex. 3 0.7 part | 6.0 | 9.4 | 14.7 | 20.7 | 24.9 | 34.4 | 43.1 | 53.9 | 71.8 | 78.0 |
| compound of Ex. 4 0.5 part | 7.5 | 9.2 | 16.7 | 23.1 | 29.4 | 37.6 | 41.2 | 48.5 | 67.7 | 87.3 |
| compound of Ex. 5 0.5 part | 5.3 | 8.8 | 12.0 | 18.5 | 30.6 | 38.2 | 48.7 | 49.0 | 68.0 | 90.2 |
| compound of Ex. 6 0.5 part | 4.2 | 9.3 | 10.7 | 20.2 | 25.0 | 34.5 | 43.4 | 50.9 | 73.8 | 88.9 |
| compound of Ex. 7 0.5 part | 11.6 | 14.6 | 24.1 | 23.3 | 29.4 | 37.0 | 49.2 | 65.3 | 99.6 | 120.4 |
| compound of Ex. 8 0.5 part | 8.0 | 18.2 | 29.0 | 32.2 | 36.2 | 48.8 | 65.1 | 72.6 | 96.9 | 125.0 |

EXAMPLE 12

(Light-stabilising action in transparent PVC)

A dry blend consisting of one of the formulations indicated in Tables 5 and 6 below is rolled for 5 minutes at 190° C. on a roller mill. From the rolled sheet obtained 0.5 mm panels are prepared in 1 minute in a hydraulic press at 180° C./200 bar.

These panels are exposed to light $\gamma > 290$ nm. The progress of the light-induced degradation is assessed according to the degree of yellowing (Yellowness Index of ASTM D 1925-70). The results are shown in Tables 5 and 6.

TABLE 5

| (a) modified PVC (K value 68) | | | 100 parts | | |
|---|---|---|---|---|---|
| epoxidised soybean oil | | | 2 parts | | |
| compound of Ex. 1 | | | 1.5 parts | | |
| Exposure time (hours) | 0 | 48 | 96 | 144 | 168 |
| YI | 15.7 | 16.1 | 16.8 | 17.5 | 17.4 |

| (b) modified PVC (K value 68) | | 100 parts |
|---|---|---|
| epoxidised soybean oil | | 2 parts |
| | YI after exposure time (hours) | |
| Additive of the invention | 0 | 192 |
| compound of Ex. 2 1.5 parts | 15.8 | 18.9 |
| compound of Ex. 3 1.5 parts | 18.1 | 20.0 |
| compound of Ex. 4 1.5 parts | 28.3 | 31.2 |
| compound of Ex. 5 1.5 parts | 21.2 | 23.1 |
| compound of Ex. 6 1.5 parts | 24.6 | 27.5 |
| compound of Ex. 7 1.5 parts | 32.0 | 31.5 |
| compound of Ex. 8 1.5 parts | 29.8 | 30.8 |
| compound of Ex. 9 1.5 parts | 36.5 | 34.6 |

TABLE 6

| modified PVC (K value 68) | | | 100 parts | |
|---|---|---|---|---|
| epoxidised soybean oil | | | 2 parts | |
| thermostabiliser (A, C, E, G or I) or a mixture of the compound of Example 1 1/1 parts and thermostabiliser (B, D, F, H or J) | | | 2 parts | |
| Stabilisers | YI after exposure time (hours) | | | |
| | 0 | 48 | 120 | 168 |
| A | 9.6 | 69.4 | 84.6 | 89.3 |
| B | 12.1 | 14.5 | 16.4 | 17.4 |
| C | 26.1 | 38.0 | 57.2 | 69.2 |
| D | 25.1 | 25.5 | 28.1 | 31.3 |
| E | 21.9 | 56.6 | 85.0 | 101.0 |
| F | 15.8 | 17.3 | 19.1 | 20.1 |
| G | 14.0 | 36.8 | 57.2 | 68.9 |
| H | 15.0 | 17.9 | 20.2 | 20.2 |
| I | 10.8 | 84.8 | 105.8 | 113.0 |
| J | 11.5 | 34.3 | 40.4 | 41.1 |
| K | 12.8 | | 88.3 | |
| L | 14.1 | | 15.6 | |
| M | 3.9 | | 49.0 | 52.8 |
| N | 17.4 | | 23.7 | 24.7 |

A = organotin mercaptide stabiliser[1]
B = mixture of the organotin mercaptide stabiliser and the compound of Example 1
C = dibutyltin maleate
D = mixture of dibutyltin maleate and the compound of Example 1
E = calcium/zinc thermostabiliser[2]
F = mixture of the calcium/zinc thermostabiliser and the compound of Example 1
G = barium/cadmium stabiliser[3]
H = mixture of the barium/cadmium stabiliser and the compound of Example 1
I = antimony tris-thioglycolic acid 2-ethylhexyl ester
J = mixture of antimony tris-thioglycolic acid 2-ethylhexyl ester and the compound of Example 1
K = barium/zinc stabiliser[4]
L = mixture of the barium/zinc stabiliser and the compound of Example 1
M = aminocrotonate stabiliser[5]
N = mixture of the aminocrotonate stabiliser and the compound of Example 1

[1]Mixture of dioctyltin dithioglycolic acid 2-ethylhexyl ester and octyltin tris-thioglycolic acid 2-ethylhexyl ester
[2]Commercially available as Irgastab CZ 121 ®

EXAMPLE 13

(Light-stabilising action in pigmented PVC)

Panels are prepared and tested as described in Example 12. The results are shown in Table 7.

TABLE 7

| modified PVC (K value 68) | | | 100 parts | |
|---|---|---|---|---|
| titanium dioxide | | | 6 parts | |
| | YI after exposure time (hours) | | | |
| Stabilisers | 0 | 144 | 288 | 384 | 696 |
| 2 parts of organotin mercaptide[1] | 4.1 | 7.7 | 14.3 | 20.8 | 42.5 |
| 1.5 parts of the compound of Ex. 1<br>2.0 parts of epoxidised soybean oil | 8.3 | 8.4 | 8.9 | 9.0 | 12.6 |
| 1 part of organotin mercaptide[1]<br>2 parts of the compound of Ex. 1<br>2 parts of epoxidised soybean oil | 5.1 | 6.6 | 8.5 | 9.1 | 15.7 |

[1] Mixture of dioctyltin dithioglycolic acid 2-ethylhexyl ester and octyltin tris-thioglycolic acid 2-ethylhexyl ester.

EXAMPLE 14

(Light-stabilising action in modified PVC)

A dry blend consisting of the formulation indicated in Table 8 below is processed for 15 minutes at 175°–180° C. on a two-roll mill. The rolled sheet obtained is subsequently moulded for 3 minutes at 200° C. to samples of 1 mm thickness. The sheets are irradiated in the Xenotest 1200 and the Δ Yellowness Index (YI) is determined according to ASTM D 1925. The results are shown in Table 8.

TABLE 8

| impact-resistant PVC (Vestolit HIS 6882 ®) modified with ethylene vinyl acetate | 100 parts |
|---|---|
| cadmium laurate | 1.4 parts |
| barium laurate | 0.5 part |
| n-octadecyl-3-(4-hydroxy-3,5-di-tert-butylphenyl) propionate | 0.1 part |
| didecylphenyl phosphite | 0.5 part |
| epoxidised soybean oil | 1 part |
| Additive of the invention | Hours required until Δ YI = 20 |
| none | 140 |
| 1% of the compound of Example 1 | 950 |

EXAMPLE 15

(Ageing stability of polyacetal)

50 g of polyacetal copolymer (Hostaform C ®) are mixed with 0.5 g of 1,8-bis[3-(3-tert-butyl-4-hydroxy-5-methylphenyl)-propionyloxy]-3,6-dioxa-octane, 0.15 g of calcium stearate and 0.25 g of the compound indicated in Table 9, and the mixture is subsequently plasticated for 7 minutes at 190° C. in a Brabender plastograph. The hot mixture is then moulded in a cold press to a 3–5 mm article. By further moulding (3 minutes at 190° C.) 1 mm sheets (panels) are prepared. The panels are hung in a circulating air oven which has been preheated to 140° C. The time which is required to achieve a Δ Yellowness Index (YI) of 20 is indicated in Table 9.

TABLE 9

| Additive of the invention | Hours required until Δ YI[*] = 20 |
|---|---|
| none | 57 |
| compound of Example 1 | 73 |

[*] acc. to ASTM D 1925

EXAMPLE 16

(Light-stabilising action in polyurethane)

The stabilisers listed in Table 10 are dissolved with stirring at 45° C. in 100 parts of Bayflex BS 577 ®(=polyetherol+activator+propellant+white paste). The solution is homogeneously mixed with 41 parts of Desmodur PF ®(=isocyanate) for 12 seconds in a mixer (1000 rpm). The mixture is immediately poured into a closeable mould at room temperature. After half an hour the foam block can be removed. Foam cut-offs with a closed surface are used for testing. The samples are irradiated in the Xenotest 150 and the Δ Yellowness Index (YI) is determined in accordance with ASTM D 1925. The results are indicated in Table 10.

TABLE 10

| Stabiliser | Hours required until Δ YI = 20 |
|---|---|
| control | 47 |
| 0.25% X[*] | 46 |
| 0.25% X[*] + 0.5% of the compound of Example 1 | 85 |

[*] X = 1,8-bis[3-(3-tert-butyl-4-hydroxy-5-methylphenyl)propionyloxy]-3,6-dioxa-octane.

EXAMPLE 17

(Light-stabilising action in flame-proofed acrylonitrile butadiene styrene)

0.5 part of the compound indicated in Table 11 is mixed on a two-roll mill with 100 parts of acrylonitrile butadiene styrene which contains 23.5% of bis(tribromophenoxy)ethane and 2.3% of $Sb_2O_3$ (flame retardant).

| Operating conditions: | |
|---|---|
| Front roll: | 160° C. and 14 rpm |
| Rear roll: | 170° C. and 16 rpm |
| Rolling time: | 4 minutes |

The mixture thus obtained is moulded in 3 minutes at 180° C. to 2 mm sheets (panels) which are irradiated in a Xenotest 150. The Δ Yellowness Index is determined after various exposure times. The results are indicated in Table 11.

TABLE 11

| | Δ Yellowness Index | |
|---|---|---|
| Exposure time (hours) | Control | Compound of Ex. 1 |
| 50 | 10 | 4.4 |
| 100 | 15 | 7.4 |
| 250 | 28 | 18.4 |

What is claimed is:
1. A compound of formula I

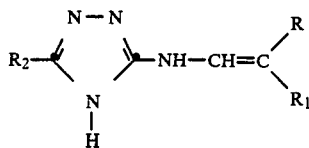 (I)

wherein R is —COOCH₃, —COOC₂H₅ or methyl, $R_1$ is —COOR₃, $R_2$ is hydrogen, methyl or ethyl and $R_3$ is $C_1$-$C_{22}$alkyl with the proviso that when $R_2$ is hydrogen, R and $R_1$ are not both —COOC₂H₅.

2. A compound according to claim 1 of formula I, wherein $R_2$ is hydrogen.

3. A compound according to claim 1 of formula I, wherein $R_2$ is hydrogen and $R_3$ is $C_1$-$C_{14}$alkyl.

4. A compound according to claim 3, wherein $R_3$ is methyl or ethyl.

5. A compound according to claim 1 of the formula

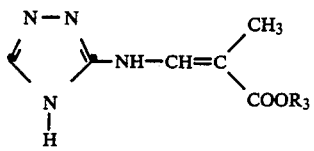 (III)

wherein $R_3$ is methyl, ethyl, n-butyl, isobutyl, 2-ethylhexyl or isotridecyl.

6. A compound according to claim 1 of the formula

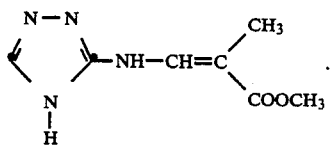

7. A stabilized composition which comprises
(a) an organic polymer, and
(b) 0.01 to 5% by weight, based on the stabilized polymer, of at least one compound of formula I

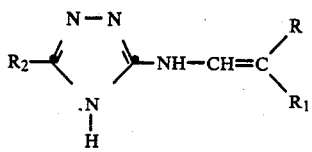 (I)

wherein R is —COOCH₃, —COOC₂H₅ or methyl, $R_1$ is —COOR₃, $R_2$ is hydrogen, methyl or ethyl and $R_3$ is $C_1$-$C_{22}$alkyl.

8. A composition according to claim 7 wherein component (a) is a thermoplastic moulding composition based on poly(vinyl chloride) or a copolymer of vinyl chloride, and component (b) is 0.1 to 5% by weight of a compound of formula I.

9. A composition according to claim 7 wherein component (b) is a compound of the formula

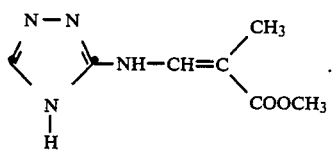

10. A composition according to claim 7 wherein component (b) is a compound of the formula

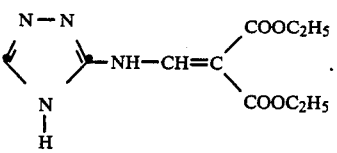

11. A moulding composition according to claim 8, which composition additionally contains one or more conventional PVC stabilisers and/or additives selected from the group consisting of epoxy compounds, phosphites, thiophosphates, thiophosphites, polyols, mercaptans, nitrogen-containing stabilisers, 1,3-diketo compounds, organometal compounds of metals of the second main and auxiliary group of the Periodic Table, basic salts of metals of the second to fourth main and auxiliary groups of the Periodic Table and organotin compounds or organic antimony compounds, antioxidants, light stabilisers, pigments and lubricants.

12. A moulding composition according to claim 11, which composition contains as conventional additive at least one epoxy compound and/or metal carboxylate or metal phenolate of a metal of the second main group of the Periodic Table.

13. A moulding composition according to claim 12, which composition additionally contains at least one phosphite.

14. A moulding composition according to claim 12, which composition additionally contains at least one zinc carboxylate or cadmium carboxylate or organotin compound.

15. A moulding composition according to claim 14, which composition additionally contains at least one phosphite.

* * * * *